United States Patent

Reuschling et al.

[11] Patent Number: 4,916,228
[45] Date of Patent: Apr. 10, 1990

[54] PROCESS FOR THE PREPARATION OF 1-HYDROXY-2-PYRIDONES

[75] Inventors: Dieter Reuschling, Butzbach; Bengt-Thomas Gröbel, Bad Soden am Taunus, both of Fed. Rep. of Germany

[73] Assignee: Hoechst Aktiengesellschaft, Frankfurt am Main, Fed. Rep. of Germany

[21] Appl. No.: 80,085

[22] Filed: Jul. 31, 1987

[30] Foreign Application Priority Data

Aug. 2, 1986 [DE] Fed. Rep. of Germany ....... 3626210

[51] Int. Cl.$^4$ .................. C07D 213/89; C07D 213/63
[52] U.S. Cl. ................................. 546/290; 546/301; 546/302; 546/303
[58] Field of Search ................ 546/290, 301, 302, 303
[56] References Cited

U.S. PATENT DOCUMENTS

| 3,269,904 | 8/1966 | Bernstein et al. | 546/290 |
| 3,883,545 | 5/1975 | Lohaus et al. | 546/290 |
| 3,968,118 | 7/1976 | Lohaus et al. | 546/283 |
| 3,972,888 | 8/1976 | Lohaus et al. | 546/283 |
| 4,797,409 | 1/1989 | Lohaus et al. | 514/345 |

FOREIGN PATENT DOCUMENTS

| 0241918 | 10/1987 | European Pat. Off. | 546/290 |
| 1795270 | 12/1971 | Fed. Rep. of Germany | 546/290 |
| 2214608 | 10/1973 | Fed. Rep. of Germany | 546/290 |

OTHER PUBLICATIONS

A. Weissberger, The Chemistry of Heterocyclic Compounds, vol. 17, p. 96.
A. Weissberger, The Chemistry of Heterocyclic Compounds, pp. 178–179 & pp. 284–285.

Primary Examiner—Richard A. Schwartz
Assistant Examiner—J. Richter
Attorney, Agent, or Firm—Finnegan, Henderson, Farabow, Garrett and Dunner

[57] ABSTRACT

1-Hydroxy-2-pyridones of the formula I

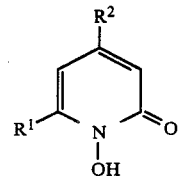

in which
$R^1$ = an organic radical and
$R^2$ = H or an organic radical,
are prepared by reacting a pyrone of the formula II

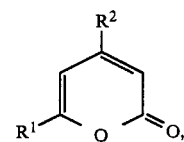

in which $R^1$ and $R^2$ have the same meaning as in formula I, with a hydroxylammonium salt in the presence of at least one alkali metal carbonate and/or hydrogen carbonate.

The compounds of the formula I have a biological activity—in particular an antibacterial and antimycotic activity.

13 Claims, No Drawings

PROCESS FOR THE PREPARATION OF 1-HYDROXY-2-PYRIDONES

1-Hydroxy-2-pyridone is the compound of the formula I (see claim 1) in which $R^1$ and $R^2$ are hydrogen, and is the basis for a number of valuable substances having an antibacterial and antimycotic activity (cf. U.S. Pat. No. 3,269,904, German Pat. No. 1,795,270 and German Pat. No. 2,214,608). Such biologically active substances are, for example, 1-hydroxy-4-methyl-6-(2,4,4-trimethyl pentyl)-2-pyridone, 1-hydroxy-4-methyl-6-cyclohexyl-2-pyridone and 1-hydroxy-4-methyl-6-[4-(4-chlorophenoxy)phenoxymethyl]-2-pyridone.

1-Hydroxy-2-pyridones are expediently prepared by the process described in German Pat. No. 2,214,608 by reacting appropriate 2-pyrones with hydroxylamine or one of its salts in the presence of an—optionally substituted—aminopyridine or imidazole. The aminopyridine or imidazole are advantageously employed in this reaction in an at least equimolar amount, relative to the hydroxylammonium salt. The temperature range specified is temperatures between room temperature and 150° C., preferably between 50° and 120° C. In the reaction, the ring oxygen atom of the 2-pyrone is replaced by the N-OH group.

In the example (No. 9) given in German Pat. No. 2,214,608 for the preparation of 1-hydroxy-4-methyl-6-(2,4,4-tri methylpentyl)-2-pyridone, 4-methyl-6-(2,4,4-trimethylpentyl)-2-pyrone is reacted with hydroxylamine hydrochloride for 43 hours at 70° C. in the presence of 2-aminopyridine, a yield of 67% of the desired pyridone then being obtained after conventional work-up. This protracted process has the further disadvantage that it is necessary to use in it considerable amounts of relatively valuable and expensive aminopyridines and/or imidazoles, which must be recovered when the reaction is complete due to their value and also for environmental protection reasons. Although it is stated in German Pat. No. 2,214,608 that some of the valuable amine compounds can be replaced by other acid acceptors of an organic or inorganic nature, this replacement occasionally leads to noticeable slowing of the reaction and also to complication of recovery of the amine.

It has now been found that it is possible to improve the known process without significantly impairing the reaction result by using alkali metal carbonates and/or hydrogen carbonates in place of the amine compounds.

The invention thus relates to a process for the preparation of 1-hydroxy-2-pyridones of the general formula I (see Patent claim 1) by reacting pyrones of the formula II (see Patent claim 1) with a hydroxylammonium salt in the presence of basic compounds, wherein the basic compounds used are alkali metal carbonates and/or hydrogen carbonates in an amount which is at least equivalent to that of the hydroxylammonium salt.

$R^1$ denotes an optionally branched, at most olefinically monounsaturated aliphatic hydrocarbon radical having 1 to 17 carbon atoms, a cycloalkyl radical having 3 to 8, preferably 6, carbon atoms in the ring and which may in addition carry 1 to 2 alkyl groups in each case having 1 to 3 carbon atoms, in particular methyl, and is bonded to the pyridone ring either directly or via a methylene or ethylene group, or a phenyl or phenylalkylmethyl radical which is unsubstituted or substituted in the aromatic ring by 1 to 3 alkyl, unsubstituted or substituted benzyl, alkoxy, unsubstituted or substituted phenoxy groups or halogen atoms, and $R^2$ denotes hydrogen, an at most olefinically monounsaturated low-molecular weight (i.e. having 1 to 6 carbon atoms) aliphatic hydrocarbon radical or a benzyl radical. Benzyl groups included in the radical $R^1$ or $R^2$ as substituent may be substituted in the same fashion as described above for the phenyl radicals. Of the radicals $R^1$ and $R^2$ which contain the phenyl ring, those are preferred in which this phenyl ring is unsubstituted or only monosubstituted or disubstituted. Preferred of the radicals mentioned for $R^2$ are alkyl radicals having 1 to 4, in particular 1 or 2, carbon atoms, and of the alkenyl radicals those having 2, 3 or 4 carbon atoms.

The hydroxylammonium salt must naturally be employed in equimolar amounts, relative to the 2-pyrone to be reacted; however, it may also be employed in excess in order to accelerate the reaction, improved results frequently being obtained in this case. It may also be expedient to add the hydroxylamine salt in several portions in the course of the reaction.

Hydroxylammonium salts which can be used are, in principle, all possible salts of hydroxylamine, for example the chloride, the sulfate, the acetate etc. However, it is preferred that the reaction be carried out using the easily accessible hydroxylammonium sulfate.

Possible alkali metal carbonates and hydrogen carbonates are virtually all carbonates and bicarbonates of the alkali metals, i.e., for example, $Li_2CO_3$, $Na_2CO_3$, $K_2CO_3$, $NaHCO_3$ and $KHCO_3$. The carbonates and bicarbonates of sodium and potassium are preferred; $Na_2CO_3$ is particularly preferred. The alkali metal carbonates and bicarbonates can be employed individually or in virtually any mixtures. Their amount is expediently at least equivalent to the amount of hydroxylammonium salt used. For example, at least ½ mole of $Na_2CO_3$ or 1 mole of $NaHCO_3$ should be used per mole of hydroxylammonium chloride.

In order to carry out the process according to the invention, the 2-pyrone is advantageously mixed with the hydroxylammonium salt and the alkali metal carbonate and/or hydrogen carbonate, and the crystal liquor obtained is warmed until pyrone can no longer be detected; the 2-pyridone produced can be isolated directly after removing the inorganic salts—or, better still, as the salt of an organic base, for example as the ethanolamine salt.

The temperature range in which the process according to the invention is carried out is significantly narrower than that for the process according to German Pat. No. 2,214,608. The maximum temperature should under no circumstances exceed 120° C. The reaction temperature is expediently above 50° and preferably between about 60° and 105° C.

It is also possible to add inert solvents or diluents. However, this is generally not necessary, but is preferred. This is in contrast to the process of German Pat. No. 2,214,608, in which such solvents and diluents were not co-used in any of the 14 examples. In the process according to the invention, the solvents and diluents are generally only added in small amounts, if at all, usually up to 50% by weight of the total reaction batch. The amount is preferably 3 to 15% by weight.

The solvents or diluents can be polar or non-polar, water-miscible or water-immiscible. The following substances can be used, for example: water, low-molecular-weight alcohols, such as methanol, ethanol, isopropanol, ethylene glycol, ethylene glycol monomethyl ether and propylene glycol, acid amides, such as dimethylformamide and diethylformamide, esters, such as ethyl acetate, ethers, such as diisopropyl ether, chlorinated hydrocarbons, such as chlorobenzene, nitriles, such as acetonitrile, and hydrocarbons of an aliphatic, cycloaliphatic or aromatic nature.

Compared to the process of German Pat. No. 2,214,608, the process according to the invention is distinguished, as a consequence of the replacement of expensive amine compounds by cheap and inexpensive alkali metal carbonates and hydrogen carbonates, not only by increased economic efficiency, but also by the particular advantages that the basic, environmentally-polluting compounds and their recovery and complete removal from the reaction batch after the reaction can be omitted and that, in some cases, shorter reaction times are also achieved. In addition, it should be taken into account that recovery of the basic compounds mentioned was only possible with acceptance of considerable losses, which led to further environmental pollution. Somewhat reduced yields do not seriously affect the increased economic efficiency of the process since, after all, the outlay for the amine compounds and the losses which had to be accepted when they were used do not arise in the present process.

The invention is illustrated by the following examples.

EXAMPLES 1-9) Preparation of 1-hydroxy-4-methyl-6-(2,4,4-trimethylpentyl)-2-pyridone (ethanolamine salt)

1) 33.5 g (150 mmol) of 4-methyl-6-(2,4,4-trimethylpentyl)-2-pyrone (99% purity), 29.8 g (429 mmol) of hydroxylammonium chloride and 22.7 g (214.5 mmol) of sodium carbonate are combined and warmed at 95° C. for 8 hours with stirring. 100 ml of ethyl acetate are subsequently added and the mixture is cooled to room temperature. The solid products are filtered off under suction and washed with 240 ml of ethyl acetate. After distillation (amount of distillate 100 ml) at about 50° C., 8.5 ml (142 mmol) of ethanolamine are added to the ethyl acetate phase. After seeding, the solution is allowed to cool for crystallization. The crystals are filtered off under suction, washed with a little cold ethyl acetate and dried. The yield of 1-hydroxy-4-methyl-6-(2,4,4-trimethylpentyl)-2-pyridone (ethanolamine salt) is 24.6-26.8 g (55-60%). Melting point 123°-6° C.

(2) 35.2 g (214.6 mmol) of hydroxylammonium sulfate are used in place of hydroxylammonium chloride, with an otherwise identical procedure; otherwise as Example 1. Yield 25-26.9 g (56-60.1%). Melting point 123°-6° C.

3-7) 447 g (2 mol) of 4-methyl-6-(2,4,4-trimethylpentyl)-2-pyrone (99% purity), 479 g (2.86 mol) of hydroxylammonium sulfate (98% purity), 306.2 g (2.86 mol) of sodium carbonate (99% purity) and a solvent or diluent (see table) are combined and warmed at 95° C. for 20 hours with stirring. 2,000 ml of ethyl acetate are added to the still-warm solution, and the solid is filtered off under suction and washed with 1,000 ml of ethyl acetate. The filtrate is subsequently extracted by stirring twice with 500 ml of water in each case. Drying is effected by removing 1,000 ml of ethyl acetate from the ethyl acetate solution by distillation. In Examples 3 and 5 to 7, 113 ml (=1.89 mol) of ethanolamine, and in Example 4, 143 ml (2.39 mol) of ethanolamine, are then added to the distillation residue (reaction product+2,000 ml of ethyl acetate) at about 50° C.; after seeding, the solution is allowed to cool for crystallization. The crystals are filtered off under suction, washed with 200 ml of cold ethyl acetate and dried.

| Example | Solvent or diluent | | $C_{14}H_{23}NO_2$·ethanolamine |
|---|---|---|---|
| | (g) | [mol] | [%] |
| 3 toluene | 410 | 5 | 49.5 |
| 4 HO-pyd.(a) | 118.7 | 0.5 | 50(b) |
| 5 H$_2$O | 4.5 | 0.25 | 54 |
| 6 H$_2$O | 18 | 1 | 53 |
| 7 H$_2$O | 36 | 2 | 53.5 |

(a) HO-pyd. = 1-hydroxy-4-methyl-6-(2,4,4-trimethylpentyl)-2-pyridone
(b) after stripping off 0.5 mol which was used as solvent.

8) 447 g (2 mol) of 4-methyl-6-(2,4,4-trimethylpentyl)-2-pyrone (99% purity), 119.7 g (0.71 mol) of hydroxyammonium sulfate (98% purity), 4.5 ml (0.25 mol) of water and 306.2 g (2.86 mol) of sodium carbonate (99% purity) are combined and warmed to 95° C. with stirring. At intervals of 60 minutes, 3 further portions each of 119.7 g (0.71 mol) of hydroxylammonium sulfate are added. The mixture is stirred at 95° C. for a total of 20 hours. The still-warm solution is worked up as in Example 3. Yield 346.1 g (58%); melting point 124.7° C.

(9A) 447 g (2 mol) of 4-methyl-6-(2,4,4-trimethylpentyl)-2-pyrone (99% purity), 83.7 g (0.5 mol) of hydroxylammonium sulfate (98% purity), 4.5 ml (0.25 mol) of water and 214.1 g (2 mol) of sodium carbonate (99% purity) are combined and warmed to 95° C. with stirring. At intervals of 60 minutes, 3 further portions each of 83.7 g (0.5 mol) of hydroxylammonium sulfate are added. The mixture is stirred at 95° C. for a total of 20 hours. Work-up is effected as in Example 3. Yield 343 g (57.5%); melting point 123°-6° C.

(9B) Isolation of 1-hydroxy-4-methyl-6-(2,4,4-trimethylpentyl)-2-pyridone from its ethanolamine salt: 298.4 g (1 mol) of 1-hydroxy-4-methyl-6-(2,4,4-trimethylpentyl)-2-pyridone ethanolamine salt are slurried in 700 ml of ethyl acetate, and 1.1 mol of 2.5N hydrochloric acid are added at room temperature. A clear solution is obtained after a short time. The ethyl acetate phase is carefully separated off and evaporated directly without further treatment. As the residue, 1-hydroxy-4-methyl-6-(2,4,4-trimethylpentyl)-2-pyridone is obtained as a white crystalline powder. Yield 234 g (98.6%); melting point 107°-110° C.

10-13) Preparation of 1-hydroxy-4-methyl-6-cyclohexyl-2-pyridone (ethanolamine salt)

(10+11) In each case, 192 g (1 mol) of 4-methyl-6-cyclohexyl02-pyrone, 239.5 g (1.43 mol) of hydroxylammonium sulfate and 153.1 g (1.43 mol) of sodium carbonate are mixed, on the one hand, with 30 ml of toluene (Example 10) or with 30 ml of methylcyclohexane (Example 11), warmed slowly to 90°-95° C. and kept at this temperature for 8 hours. While still warm, 1,000 ml of ethyl acetate are added, and the solid is filtered off under suction and washed with 500 ml of ethyl acetate. The filtrate is subsequently washed with saturated sodium bicarbonate solution until free of acid. Drying is effected by removing 500 ml of ethyl acetate from the ethyl acetate solution by distillation. 56.5 ml (0.94 mol) of ethanolamine are then added to the distillation residue at about 50° C.; after seeding, the solution is allowed to cool for crystallization. The crystals are filtered off under suction, washed with 100 ml of cold ethyl acetate and dried. The yield of 1-hydroxy-4-methyl-6-cyclohexyl-2-pyridone (ethanolamine salt) is 134–142 g (50–53%) in Example 10 and 134–139.5 g (50–56%) in Example 11; melting point 138°–142° C.

(12) 96 g (0.5 mol) of 4-methyl-6-cyclohexyl-2-pyrone, 29.9 g (0.179 mol) of hydroxylammonium sulfate and 19.1 g (0.179 mol) of sodium carbonate are warmed to 90°–95° C. After 60 minutes and at intervals of 60 minutes, a total of five further portions of 14.95 g (89.5 mmol) of hydroxylammonium sulfate and 9.6 g (89.5 mmol) of sodium carbonate are added. After the final addition, the mixture is stirred at 90°–95° C. for a further 90 minutes. Work-up is effected analogously to Example 10. Yield 137 g (51%); melting point 137°–140° C.

(13A) 96 g (0.5 mol) of 4-methyl-6-cyclohexyl-2-pyrone, 119.7 g (0.715 mol) of hydroxylammonium sulfate and 76.6 g (0.715 mol) of sodium carbonate are warmed at 95° C. for 6.5 hours. After cooling, the reaction mixture is taken up in 500 ml of water and 500 ml of ethyl acetate, and the organic phase is separated off and washed with saturated sodium hydrogen carbonate solution until free of acid. The organic phase is subsequently dried over sodium sulfate, and 28.3 ml (0.47 mol) of ethanolamine are added to the filtrate at about 50° C. The substance which crystallizes on cooling is filtered off under suction, washed with 50 ml of cold ethyl acetate and dried. Yield 139 g (52%); melting point 139°–142° C.

(13B) Isolation of 1-hydroxy-4-methyl-6-cyclohexyl-2-pyridone from its ethanolamine salt: 268.4 g (1 mol) of 1-hydroxy-4-methyl-6-cyclohexyl-2-pyridone ethanolamine salt are slurried in 700 ml of ethyl acetate, and 1.1 mol of 2.5N hydrochloric acid are added at room temperature. A clear solution is obtained after a short time. The ethyl acetate phase is carefully separated off and evaporated directly without further treatment. As the residue, 1-hydroxy-4-methyl-6-cyclohexyl-2-pyridone is obtained as a white crystalline powder. Yield 203 g (98%); melting point 143° C.

We claim:

1. A process for the preparation of 1-hydroxy-2-pyridones of the formula I

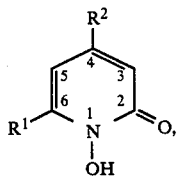

in which
R$^1$ denotes an at most olefinically monounsaturated aliphatic hydrocarbon radical having 1 to 17 carbon atoms, a cycloalkyl radical having 3 to 8 carbon atoms in the ring and which can carry in addition 1 to 2 alkyl groups in each case having 1 to 3 carbon atoms and which is bonded to the pyridone ring either directly or via a methylene or ethylene group, or a phenyl or phenylalkyl radical which is unsubstituted or substituted in the aromatic ring by 1 to 3 alkyl, benzyl, alkoxy, phenoxy or halogen atoms, where the benzyl or phenoxy groups included as substituent may be substituted in the same fashion, R$^2$ denotes hydrogen, and at most olefinically monounsaturated aliphatic hydrocarbon radical having 1 to 6 carbon atoms or a benzyl radical which is unsubstituted or may be substituted in the same fashion as in the case of R$^1$, by reacting a pyrone of the formula II

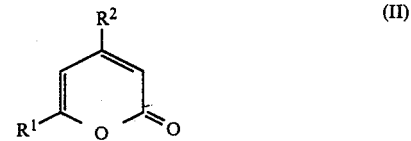

with a hydroxylammonium salt in the presence of basic compounds at a temperature not exceeding 120° C., wherein the basic compounds used are alkali metal carbonates or hydrogen carbonates in an amount which is at least equivalent to that of the hydroxylammonium salt.

2. The process as claimed in claim 1, wherein the cycloalkyl radical is a cyclohexyl radical.

3. The process as claimed in claim 1, wherein the cycloalkyl radical contains, in addition, methyl as substituent.

4. The process as claimed in claim 1, wherein R$^2$ contains at most 4, carbon atoms.

5. The process as claimed in claim 1, wherein the radicals R$^1$ and R$^2$ which contain the phenyl ring are unsubstituted or carry at most 2 substituents.

6. The process as claimed in claim 1, wherein the hydroxylammonium salt used is hydroxylammonium sulfate.

7. The process as claimed in claim 1, wherein the alkali metal carbonates or hydrogen carbonates used are those of sodium or potassium.

8. The process as claimed in claim 1, wherein the process is carried out at a temperature from 50° to 120°.

9. The process as claimed in claim 1, wherein the process is carried out in the presence of a solvent or diluent, which is preferably present in an amount up to 50% by weight of the total reaction batch.

10. The process as claimed in claim 9, wherein the solvent or diluent is present in an amount from 3 to 15% by weight of the total reaction batch.

11. The process as claimed in claim 8, wherein the process is carried out at a temperature from 60° to 105° C.

12. The process as claimed in claim 7, wherein the alkali metal carbonate is sodium carbonate.

13. The process as claimed in claim 4, wherein R$^2$ contains 1 or 2 carbon atoms.

* * * * *

UNITED STATES PATENT AND TRADEMARK OFFICE
CERTIFICATE OF CORRECTION

PATENT NO. : 4,916,228
DATED : April 10, 1990
INVENTOR(S) : Dieter Reuschling et al.

It is certified that error appears in the above-identified patent and that said Letters Patent is hereby corrected as shown below:

Claim 4, before "carbon", delete ",".

Claim 8, after "120°", add --C--.

Signed and Sealed this

Twentieth Day of August, 1991

Attest:

HARRY F. MANBECK, JR.

*Attesting Officer*  *Commissioner of Patents and Trademarks*